United States Patent [19]

Van Sickle

[11] Patent Number: 4,983,777
[45] Date of Patent: Jan. 8, 1991

[54] DIISOPROPYLBIPHENYL MONO- AND DI-HYDROPEROXIDES, PROCESS FOR THE PREPARATION THEREOF, AND COMPOUNDS DERIVED THEREFROM

[75] Inventor: Dale E. Van Sickle, Kingsport, Tenn.

[73] Assignee: Eastman Kodak Company, Rochester, N.Y.

[21] Appl. No.: 431,957

[22] Filed: Nov. 6, 1989

Related U.S. Application Data

[63] Continuation of Ser. No. 189,931, May 3, 1988, abandoned.

[51] Int. Cl.$^5$ ............................................. C07C 409/00
[52] U.S. Cl. ...................................... 568/568; 568/564
[58] Field of Search ................................ 568/568, 564

[56] References Cited

FOREIGN PATENT DOCUMENTS 63-309858 12/1988 Japan ................................... 568/568
63-309860 12/1988 Japan ................................... 568/568

Primary Examiner—Bruce Gray
Attorney, Agent, or Firm—J. Frederick Thomsen; William P. Heath, Jr.

[57] ABSTRACT

Disclosed is a process for the oxidation of 4,4'-diisopropylbiphenyl which gives an excellent ratio of dihydroperoxide to monohydroperoxide and a low amount of other oxygenated compounds. The dihydroperoxide can be converted, by known procedures, to 4,4'-biphenyldiol or a diester thereof which are valuable monomers used in the manufacture of high performance polyesters. Certain of the disclosed compounds such as the dihydroperoxide, monohydroperoxides and diesters are new compositions of matter.

2 Claims, No Drawings

DIISOPROPYLBIPHENYL MONO- AND DI-HYDROPEROXIDES, PROCESS FOR THE PREPARATION THEREOF, AND COMPOUNDS DERIVED THEREFROM

This is a continuation of copending application Ser. No. 07/189,931 filed on May 3, 1988, abandoned.

This invention concerns novel 4,4'-diisopropylbiphenyl mono- and di-peroxides and to a process for the preparation thereof by the oxidation of 4,4'-diisopropylbiphenyl. This invention also concerns certain novel hydroxy and alkanoyloxy compounds derived from the aforesaid peroxides. Another aspect of the present invention pertains to a process for the preparation of 4,4'-biphenyldiol by the oxidation of 4,4'-diisopropylbiphenyl followed by the decomposition of the dihydroperoxide formed to obtain 4,4'-biphenyldiol.

High performance polyesters, commonly referred to as liquid crystal polyesters, utilize 4,4'-biphenyldiol (referred to herein as BPD) as a monomer in their production. Such BPD-based polyesters are used in the fabrication of cookware which is stable to microwave oven temperatures. Examples of these types of polyesters are disclosed in U.S. Pat. Nos. 3,637,595, 3,975,487 and 4,639,504.

The known processes for the preparation of BPD are disadvantageous and have caused BPD to be relatively expensive when compared to the cost of other monomers used in large volumes in the manufacture of polyesters. One process involves the sulfonation of biphenyl to the disulfonic acid wherein the 4,4'-isomer may be formed preferentially by careful adjustment of the temperature and acid concentration of the reaction mixture. The isolated 4,4'disulfonic acid is fused with potassium hydroxide to give the dipotassium salt of DHBP which then is converted to DHBP by treatment with sulfuric acid. A significant problem presented by this manufacturing route is the disposal of the large quantities of potassium sulfate which are formed.

A second manufacturing procedure of more recent origin involes an oxidative coupling reaction of 2,6-di-t-butylphenol to produce a diphenoquinone:

Reduction of the intermediate diphenoquinone gives the tetrakis(t-butyl)-4,4'-biphenyl which then must be debutylated to give the desired BPD. To be economically feasible, this process would require recovery and recycling of the isobutylene generated to a facility for the production of the 2,6-di-t-butylphenol starting material.

I have discovered that BPD may be produced economically by the autoxidation of 4,4'-diisopropylbiphenyl (DIPBP) followed by the acid-catalyzed decomposition of the 4,4'diisopropylbiphenyl dihydroperoxide formed. By carrying out the decomposition in the presence of a carboxylic acid anhydride, e.g., an anhydride of a dicarboxylic acid of 2 to 5 carbon atoms, the analogous 4,4'-bis-alkanoyloxybiphenyl (or 4,4'-biphenyl dialkanoate) can be obtained. The bis-ester is preferred in the preparation of polyesters containing BPD residues. The oxidation of 4,4'-diisopropylbiphenyl also yields 4,4'-diisopropylbiphenyl monohydroperoxide which, like the dihydroperoxide, is a new composition of matter. Other novel compounds formed by the oxidation and/or decomposition processes include 4-alkanoyloxy-4'-isopropylbiphenyl and 4-alkanoyloxy-4'-(2-hydroperoxy-2-propyl)biphenyl.

The successful oxidation of difunctional aromatic compounds such as a diisopropylarene is less certain than is the oxidation of monofuntional compounds such as the oxidation of cumene to cumene hydroperoxide since in the former double peroxidation is necessary. An example of a diisopropylarene which is inert to oxidation is 1,2-diisopropylbenzene which is not converted to hydroperoxide. In contrast, the 1,3- and 1,4-isomers of diisopropylbenzene can be oxidized to the mono- and then to the dihydroperoxides. In the oxidation of difunctional compounds the oxidation must be carried out to a relatively high conversion so that a significant amount of dihydroperoxide will be obtained. The achievement of a high conversion requires that the oxidation not become self-retarding at an early stage and that the desired dihydroperoxide be efficiently seperated from the intermediate monohydroperoxide. I have found that the oxidation of 2,6-diisopropylnaphthalene tends to become self-retarding which severely limits the amount of the dihydroperoxide which can be built up in the system. According to the literature (U.S. Pat. No. 4,503,262), the catalytic oxidation of 2,6-diisopropylnaphthalene to its dihydroperoxide can be improved by conducting the oxidation in heptane rather then benzene.

U.S. Pat. No. 4,326,088 suggests the conversion of 4,4'-diisopropyldiphenylether (DIPDE) to the analagous 4,4'-dihydroxydiphenylether by the oxidation of the former followed by decomposition of the peroxides formed. However, no dihydroperoxide was isolated from the crude oxidation product and the acid-catalyzed rearrangement step was performed only in the presence of a mixture of the mono- and dihydroperoxides of DIPDE. The oxidative conversion of the DIPDE was relatively low, e.g., 23–34 percent, and, thus, the amount of dihydroperoxide formed, relative to the amount of intermediate monohydroperoxide, apparently was quite small, i.e., the acid-catalyzed rearrangement of the crude hydroperoxide mixture would be expected to yield a mixture of phenolic compounds containing a major amount of 4-isopropyl-4'-hydroxydiphenylether and a minor amount of the desired 4,4'-dihydroxydiphenylether. The cited patent does not disclose the separation of the monohydroxy and dihydroxy compounds.

I have found that 4,4'-diisopropylbiphenyl (DIPBP) can be readily oxidized to, sequentially, the monohydroperoxide and then the dihydroperoxide and that the two hydroperoxides can be conveniently separated by extraction and/or crystallization techniques. The desired BPD can thus be obtained in good purity and reasonable conversion rates from the isolated dihydroperoxide by means of known acid-catalyzed rearrangement procedures. The monohydroperoxide may be recycled along with additional DIPBP for conversion to the dihydroperoxide. The rearrangement step coproduces acetetone which is used in large volumes in various chemical processes. Since the diester of BPD is preferred in some instances over BPD as a monomer in the manufacture of polyesters, the rearrangement of the dihydroperoxide preferably may be performed in the presence of a carboxylic acid anhydride to obtain the biphenyl dialkanoate, e.g., 4,4'-biphenyl diacetate.

The oxidation process provided by this invention may be carried out by intimately contacting molten 4,4'-diisopropylbiphenyl with oxygen or an oxygen-containing gas under hydroperoxide-forming conditions of temperature and pressure. Normally, the process is conducted at temperatures in the range of about 70° to 100° C. although I have found temperatures in the range of about 75° to 85° C. to give the best results. Although the laboratory work I have conducted indicates that the optimum temeperature is approximately 80°, slightly different temperatures may provide the best results when operating on a commercial scale. The pressure at which the process is performed can be varied substatially, depending on a number of factors such as, for example, the mode of operation, the oxidation rate desired, etc. While oxygen partial pressures in the range of about 3 to 150 pounds per square inch gauge (psig) may be used, oxygen partial pressures in the range of about 20 to 60 can be used to give good oxidation rates at reasonable oxygen supply costs.

The oxidation reaction may be accomplished using oxygen, i.e., molecular oxygen, or an oxygen-containing gas such as air or oxygen-enriched air. The oxidation may utilize a static head of oxygen-containing gas in combination with means for agitating the reaction mixture or, preferably, the oxygen-containing gas is fed continuously to a pressure vessel containing DIPBP through a sparger which provides for intimate contact between the gas and liquid phases. In the latter mode of operation, condensible materials contained in the off-gas may be collected and returned, continuously or intermittently, to the oxidizer. The process requires the presence of a free radical initiator such as 1,1'-azobis(1-cyanocyclohexane), 2,2'-azobis(2-methylpropionitrile), 2-t-butylazo-2-cyanopropane and the like and peroxides, e.g., 4,4'-diisopropylbiphenyl monohydroperoxide, 4-acetoxy-4'-isopropylbiphenyl hydroperoxide, benzoyl peroxide di-t-butyl peroxide, etc. The amount of initiator can be varied over a wide range depending on the oxidation rate and "kinetic chain length" desired and the particular initiator employed. Generally, molar ratios of initiator to DIPBP in the range of 0.005 to 0.1 may be used. Due to its decomposition rate, i.e., its free radical generating rate and duration, at 80° C., 1,1'-azobis(1-cyanocyclohexane) was used in the examples set forth hereinbelow. However, in commerical operations in which the monohydroperoxide of diisopropylbiphenyl is available and typically recycled to the oxidizer along with fresh DIPBP, the monohydroperoxide may serve as the initiator thus eliminating the need for an extraneous free radical initiator.

My novel oxidation process is carried out in the presence of a weak base which functions to neutralize any acids formed by the process since such acids act as catalysts for the hydroperoxide rearrangement to produce phenols which retard substantially the oxidation reaction. Examples of suitable bases include the alkali metal bicarbonates, e.g., sodium and potassium bicarbonate, the alkaline earth metal hydroxides, e.g., magnesium, calcium and barium hydroxide. The process may be carried out using molten DIPBP with or without an inert solvent. Possible solvents that may be used include benzene, chlorobenzene and diphenyl ether.

The acid rearrangement or cleavage of the hydroperoxides whereby the 2-hydroperoxy-2-propyl radicals are converted to hydroxy groups can be carried out employing any of the known and conventional procedures such as those described in U.S. Pat. Nos. 2,626,281, 2,628,983, 3,884,983, 3,927,124, 3,928,469, 3,900,423 and 3,923,908. In accordance with known procedures, the hydroperoxide is decomposed at ambient temperature in the presence of acid. Examples of suitable acids include strong mineral acids such as sulfuric acid, strong organic acids such as methanesulfonic and toluenesulfonic acid or an acidic ion exchange resin such as a sulfonated styrene-divinylbenzene resin in its hydrogen or acidic form. Other acidic rearrangement catalyst are set forth in Methoden der Organischen Chemie (Houben-Weyl), Vol. VI/1c, Part 1, Georg Thieme Verlag Stuttgart, p. 124. My invention is further illustrated by the following examples. The DIPBP used in the examples was either 97.65 pure (gas chromatography analysis) or 99% pure (twice recrystallized from isopropanol). The apparatus used consisted of a glass bulb connected to an oxygen reservoir tank by flexible metal tubing. The DIPBP reactant, base and initiator were placed in the glass bulb reactor which was then pressurized with oxygen. The bulb was shaken mechanically in a constant temperature bath (typically 80° C.) and consumption of oxygen noted by change of gauge pressure on the reservoir tank. After the desired amount of oxygen had been absorbed, the bulb was detached from the metal tubing and the product-unconsumed reactant mixture was taken up in acetone and the resulting solution was filtered for work-up and analyses. Analytical techniques used were liquid chromatography and/or titration for hydroperoxides. The reported reaction periods commenced shortly after the glass bulb containing the initial reaction mixture had been agitated in the oil bath.

EXAMPLE 1

DIPBP (12.01 g, 0.0484 mol) of 99+% purity was oxidized at 80° C. and an initial oxygen pressure of 60 psig in the presence of calcium hydroxide (0.27 g) and 1,1'-azobis(1-cyanocyclohexane) (0.208 g) for 1220 minutes. The rate of oxygen up-take initially and during a substantial portion of the oxidation period was 0.0029 mol/L/-minute. The final up-take rate was 0.0018 mol/L/-minute, 62% of the initial rate when a total of 40.2 millimoles (mmol) of oxygen had been absorbed for an excellent conversion of 79.8% (moles of molecular oxygen absorbed/moles of DIPBP initially present). The crude oxidation product contained 23.35 mmol of DIPBP monohydroperoxide, 9.08 mmol DIPBP dihydroperoxide, 0.58 mmol of hydroxyhydroperoxide (4-[2-hydroxy-2-propyl]-4'-[2-hydroperoxy-2-propyl[-biphenyl and 3.74 g of unconverted DIPBP. The total of the oxygenated products gives an oxygen accounting of 42.38 mmol, 5.5% greater than the experimentally determined quantity. No other peak in the analysis constitutes more than 0.44 area percent of the total.

This example shows that the oxidation of DIPBP results in both high conversion and selectivity, that there is negligible retardation and that a high concentration of dihydroperoxide (mono/di ratio of 2.57) can be built up for isolation and conversion to 4,4'-biphenyldiol.

EXAMPLE 2

DIPBP (12.57 g, 0.0507 mol) was oxidized at 90° C. in the presence of calcium hydroxide (0.28 g) and 1,1'-azobis(cyclohexanecarbonitile (0.154 g) over a period of 540 minutes at an initial oxygen pressure of 60 psig. The amount of oxygen which had been consumed at the conclusion of the oxidation was 33.7 mmol giving a conversion of 63.9%. The oxidate contained 19.98 mmol monohydroperoxide, 5.75 mmol dihydroperoxide and 1.39 mmol of hydroxyhydroperoxide for an accounting of 33.56 mmol oxygen or 99% of the oxygen absorbed indicating the formation of only trace amounts of other oxygenated products. This example shows that increasing the oxidation temperature to 90° C. improves reaction rate without causing excessive hydroperoxide decomposition.

EXAMPLE 3

Using the procedures described above, DIPBP was oxidized at 80° C. for 1075 minutes to achieve a conversion of 57.9%. A portion of the oxidizer product, which was 13.4 weight percent dihydroperoxide, was dissolved in 25 mL toluene and the toluene solution was extracted three times with 10 mL portions of a base solution containing 4 weight percent sodium hydroxide and 4 weight percent sodium carbonate. The extracts were combined and back extracted with three 10 mL portions of 4-methyl-2-pentanone. The ketone extracts were evaporated under vacuum and the white residue was washed with water to remove traces of the bases. The DIPBP dihydroperoxide thus obtained (0.44 g) was 96% pure and melted at 140°–142° C. A carbon-13 NMR spectrum of the material was definitive and consistent with the expected DIPBP dihydroperoxide.

EXAMPLE 4

A solution of about 0.15 g of DIPBP dihydroperoxide in 5 mL acetone containing 0.5 g of an acidic ion exchange resin (Amberlyst 15) was stirred at room temperature for three hours. The resin was filtered from the solution and the acetone was evaporated to give 0.10 g of white solid assaying 90% BPD by gas chromatography and gave a retention time equal to that of an authentic sample. The melting point of the material was 275°–280° C. and the molecular weight by field desorption mass spectroscopy was 186.

EXAMPLE 5

A solution of 0.20 g DIPBP dihydroperoxide in 5 mL acetone was added to a stirred mixture of 10 mL of acetic anhydride and 0.5 g of Amberlyst 15 resin. After one hour of stirring the solution was decanted from the resin beads and most of the acetone, acetic anhydride and acetic acid was evaporated under vacuum (20 torr) to leave 0.4 g of residue which was taken up in 4 mL of boiling ethanol. Cooling of the ethanol solution to room temperature precipitated 0.14 g of white crystals which, by gas chromatography, were 97.5% pure 4,4'-biphenyl diacetate. The gas chromatography retention time was identical to that of an authentic sample. The melting point of the product was 165°–167° C.

EXAMPLE 6

A portion (3.5 g) of the product of a DIPBP oxidation taken to 79% conversion according to a procedure analagous to those described in Examples 1 and 2 was taken up in 10 mL of diisobutylene at the boil. Upon cooling to room temperature, 0.76 g of crystals precipitated from the diisobutylene solution. The weight ratio of dihydroperoxide/monohydroperoxide had been increased from 19.6/42.2 in the oxidation product to 61.0/31.8 in the crystalline product. An aliquot (0.20 g) of the crystalline product was taken up in acetone and added to a stirred mixture of 10 mL of acetic anhydride and 0.5 g of Amberlyst 15 resin. After 30 minutes of stirring, the solution was decanted from the resin beads which were washed with acetone. The combined reaction mixture and acetone washings were evaporated under vacuum to give 0.29 g of crystalline residue. The residue was recrystalized from hot ethanol to obtain 0.10 g of crystals which assayed 92.8% 4,4'-biphenyl diacetate by gas chromatography and melted at 160°–165° C.

Thus, as demonstrated by this example, DIPBP can be concentrated by crystallization techniques and, combined with the ease of isolation and purification of the diacetate ester, a process for the production of 4,4'-biphenyl diacetate can be carried out without recourse to extraction procedures.

EXAMPLE 7

A 12.8 g portion of a DIPBP oxidation product containing 29.6 weight percent DIPBP dihydroperoxide, 42.2 weight percent DIPBP monohydroperoxide and 2.1 weight percent hydroxyhydroperoxide was taken up in 25 mL of toluene and extracted six times with 10 mL portions of aqueous 4 weight percent sodium hydroxide/4 weight percent sodium carbonate solution. The remaining toluene solution was washed with water and then evaporated under vacuum (20 torr) to give 11.17 g of product which was taken up in about 25 mL of hot methylcyclohexane. Upon cooling to room temperature, a precipitate formed and was filtered off to give 1.85 g of product which, by liquid chromatography, assayed 31.8% DIPBP dihydroperoxide, 52.1% DIPBP monohydroperoxide and 11.4% hydroxyhydroperoxide. Chilling the methylcyclohexane solution to -10° C. precipitated a substantial amount (4.16 g) of additional product which assayed 82.6% monohydroperoxide, 2.9% dihydroperoxide and 1.3% hydroxyhydroperoxide. This product was purified further by preparative liquid chromatography to give a solid which melts at 79.1° C. (DSC max). The proton NMR is consistent with the assigned structure.

A portion (1 g) of the 82.6% monohydroperoxide material was subjected to acid-catalyzed rearrangement by adding it as a solution in 10 mL of acetone to a stirred mixture of 10 mL of acetic anhydride and 0.5 g Amberlyst resin. The product solution was decanted from the resin beads and evaporated under vacuum (60° C., 20 torr) to give 1.5 g of residue from which was obtained by recrystallization from ethanol 0.5 g of 4-isopropyl-4'-biphenyl acetate which assayed approximately 90% and had a melting point of 88°–90° C. Mass spectroscopy confirmed the identity of the compound by molecular weight. The compound may be oxidized to produce 4-[2-hydroperoxy-2-propyl]-4'-biphenyl acetate which can be converted to 4,4'-biphenyldiol monoacetate.

While the invention has been described in detail with particualr reference to preferred embodiments thereof, it will be understood that variations and modifications can be effected within the spirit and scope of the invention.

I claim:

1. The compound 4,4'-diisopropylbiphenyl dihydroperoxide.

2. The compound 4,4'-diisopropylbiphenyl monohydroperoxide.

* * * * *